(12) United States Patent
Studin

(10) Patent No.: US 9,393,182 B2
(45) Date of Patent: Jul. 19, 2016

(54) ANTI-AGING PRODUCT

(75) Inventor: Joel R. Studin, Great Neck, NY (US)

(73) Assignee: Scarguard Labs, LLC, Great Neck, NY (US)

( * ) Notice: Subject to any disclaimer, the term of this patent is extended or adjusted under 35 U.S.C. 154(b) by 1538 days.

(21) Appl. No.: 12/273,258

(22) Filed: Nov. 18, 2008

(65) Prior Publication Data

US 2010/0124561 A1 May 20, 2010

(51) Int. Cl.
*A61K 8/02* (2006.01)
*A61Q 19/08* (2006.01)

(52) U.S. Cl.
CPC . *A61K 8/02* (2013.01); *A61Q 19/08* (2013.01); *A61K 2800/88* (2013.01)

(58) Field of Classification Search
CPC .................................. A61K 8/02; A61Q 19/08
USPC .......................................................... 424/401
See application file for complete search history.

(56) References Cited

U.S. PATENT DOCUMENTS

| 2,015,972 | A | 10/1935 | Sodergren |
| 2,245,738 | A | 6/1941 | Taylor |
| 2,791,324 | A | 5/1957 | Knoop et al. |
| 4,790,429 | A | 12/1988 | Fukushima |
| 5,137,178 | A | 8/1992 | Stokes et al. |
| 5,287,961 | A | 2/1994 | Herran |
| 5,616,337 | A | 4/1997 | Kasianovitz et al. |
| 5,881,869 | A | 3/1999 | Hudson |
| 5,914,116 | A | 6/1999 | Suares et al. |
| 5,935,589 | A | 8/1999 | Mukhedjee et al. |
| 6,585,984 | B1 | 7/2003 | Scott et al. |
| 6,789,945 | B2 | 9/2004 | Mobs et al. |
| 6,939,552 | B2 | 9/2005 | Ansara et al. |
| 7,186,046 | B2 | 3/2007 | Kauffmann et al. |
| 7,267,483 | B2 | 9/2007 | Nokura |
| 7,326,406 | B2 | 2/2008 | Crook et al. |
| 2006/0035924 | A1 | 2/2006 | Schmid |
| 2008/0118417 | A1 | 5/2008 | Mallory |
| 2009/0017080 | A1 | 1/2009 | Tanner et al. |

FOREIGN PATENT DOCUMENTS

| KR | 100478424 | 3/2005 |
| WO | WO9850012 | 11/1998 |

*Primary Examiner* — Gina Justice
(74) *Attorney, Agent, or Firm* — Fishman & Associates, LLC.

(57) ABSTRACT

The present invention is directed to an anti-aging product, a single use multi-chamber packaging and a method of using the anti-aging product for reducing and/or preventing age-related skin symptoms. More particularly, the present invention is directed to a single use multi-chamber packet that has at least two chambers or compartments each containing at least one portion of an anti-aging composition, wherein said portions can be combined prior to application to the skin for reducing and/or preventing age-related skin symptoms.

In another embodiment, the present invention is directed to an anti-aging kit comprising at least two or more single use multi-chamber packets, each having at a different composition for reducing and/or preventing age-related skin symptoms.

11 Claims, 4 Drawing Sheets

ANTI-AGING PRODUCT

FIELD OF THE INVENTION

The present invention is related to an anti-aging skin care composition for use in the treatment or prevention of age-related skin symptoms. More specifically, the present invention is directed to a multi-chamber packet, which contains an anti-aging skin care composition, and to anti-aging kits for use in the treatment or prevention of age-related skin symptoms.

BACKGROUND OF THE INVENTION

A soft, supple and flexible skin has a marked cosmetic appeal. As human skin ages with advancing years, the epidermis can become folded, ridged or furrowed to form wrinkles. These signal loss of youthful appearance and herald the transition to old age. Exposure to excessive doses of sunlight accelerates the transition process. Moreover, the outer layer of the epidermis known as the stratum corneum can become dry and flaky following exposure to cold weather or excessive contact with detergents or solvents.

Science has discovered a few active substances which can counter the aging process. Among these are the retinoids and the alpha-hydroxy carboxylic acids. Unfortunately these active substances can be incompatible under certain conditions. Retinol rapidly degrades in a acidic environment that may be most conducive to the alpha-hydroxys. Combinations of these actives have been reported in U.S. Pat. No. 5,935,589 (Mukhedjee et al.) which places the actives in separate emulsions within a single composition. Retinol is stabilized at a neutral pH in an oil-in-water emulsion. An alpha-hydroxy carboxylic acid such as glycolic acid is dispersed within a water-in-oil emulsion. Both of these emulsions are then carefully combined to form a single cosmetic composition. A problem for such compositions is that over time there will be leakage between the separate emulsions resulting in retinol degradation.

Treatments designed to prolong or promote youthful appearance of skin include topical applications of cosmetic preparations, lotions and moisturizers. Many skin care compositions have been created to treat wrinkles and fine lines and restore the youthful appearance of skin, and most of these are intended to improve the skin's surface characteristics, for example, to minimize environmental effects and stress on the skin, improve texture, firmness and elasticity, counteract dryness, smooth out wrinkles, minimize age spots, improve color, and increase moisture content of the skin. However, in many cases the different active ingredients used to treat the various different causes of aging can react together causing these active ingredient to degrade and/or lose their efficacy over time. As a result, it has been necessary to provide different active ingredients for the treatment of the different causes of aging in numerous bottles, each of which can be applied separately to the skin. The application of these active ingredients from numerous bottles can be cumbersome and inconvenient for the user.

A more direct solution is placement of the different actives into compositions held in separate compartments of a dispenser. Illustrative is U.S. Pat. No. 5,914,116 (Suares et al.) disclosing releasably lockable stackable jars and dual compartment pumps. These packages are designed to deliver the separate actives at different times rather than through simultaneous dosing. In U.S. Pat. No. 5,137,178 (Stokes et al.) a dual compartmented squeezable cosmetic dispenser is disclosed which allows for simultaneous extrusion of separate composition streams.

While each of the aforementioned systems have their particular advantage, they introduce certain disadvantages. Actives placed in dual stream dispensing compartments must be doubly concentrated. Only half of each stream contributes to the final dispensed combined stream concentration. For instance, delivery of 8% alpha-hydroxy carboxylic acid requires a 16% concentrated stream from an equally dispensing dual stream package. High concentration presents problems. Significant skin irritation and erythema may result from localized, non-fully mixed deposition of the stream onto the skin. Internal stability at high concentration may also be compromised. There is need for a better solution.

WO 98/50012 (Noordam et al.) discusses the problem of stabilizing a low pH emulsion of Vitamin C to prevent oxidation of the active. Stabilization is achieved by placing a relatively concentrated aqueous Vitamin C composition in one compartment of a multi-compartment dispensing system. A second compartment contains a cosmetic carrier composition. When ready for use, a small volume of the Vitamin C concentrate is dispensed alongside a larger volume of the carrier base, each being expressed from a separate compartment.

A similar approach has been disclosed by Airspray™ in product brochure literature for their Symbio dual-chamber dispenser. Two non-compatible ingredients are separated each from the other until the moment of application. The Symbio package has two separate chambers each connected to its own pump, one of the chambers being smaller and arranged to deliver a concentrate of an unstable cosmetic substance. Among the unstable substances mentioned are Vitamin A (retinol), Vitamin C (ascorbic acid) and Vitamin E (alpha-tocopherol). There is no suggestion that the larger container included any skin actives other than some enzymes and pigmentation control agents. The technology does not present a solution for delivering actives from a dual compartment in a manner that provides nearly identical stored and skin delivered concentrations. Focus is rather upon an active that is stored highly concentrated but delivered dilute.

Some ingredients used in topical products are potentially irritating, especially to people with "sensitive skin." For example, chemical skin peeling agents, such as hydroxy acids (HAs), have been proven to deliver cosmetic benefits, such as improvement in the appearance of photodamaged or naturally aged skin, skin lightening, treatment of age spots, etc. Unfortunately, their use at high concentrations may be associated with skin irritation, e.g. skin redness and stinging sensation upon application. The irritation can be ameliorated by lowering the amount of an active ingredient in the composition or by reducing the active's penetration through the skin. A serious drawback of both approaches is that the efficacy is impaired. The HA related irritation can be reduced by raising the composition's pH but this method yields reduced efficacy due to a decreased HA penetration through the skin. It is desirable to reduce or eliminate the irritation potential of HAs while maintaining their efficacy.

Besides performance in reducing signs of skin aging itself, a number of additional issues underlie the development of a successful anti-aging cosmetic formulation, such as those of skin tolerance, pleasant odor, visually appealing and pleasant feeling texture and shelf life or stability.

Accordingly, it is an object of the present invention to provide an anti-aging composition and means of packaging that may facilitate ease of use, long-term storage, and/or efficacy of the anti-aging skin care composition. Moreover, it is an object of the present invention to provide a multi-chamber packet, which contains an anti-aging skin care composition, and to an anti-aging kits which allow for safe application of an anti-aging composition for the treatment or prevention of age-related skin symptoms.

SUMMARY OF THE INVENTION

The present invention is directed to an anti-aging skin care composition and to a single use multi-chamber packaging of said composition for use in the reduction and/or prevention of age-related skin symptoms. More particularly, the present invention is directed to a single use squeezable or compressible multi-chamber packet that has at least two or more chambers or compartments each containing a portion of an anti-aging skin care composition. The skin care composition of the present invention can contain one or more active agents for the reduction and/or prevention of age-related skin symptoms, which can be combined and mixed prior to application to the skin.

In one embodiment, the present invention is an anti-aging skin care composition for reducing and/or preventing age-related skin symptoms. In accordance with this embodiment, the anti-aging composition contains one or more active agents.

In another embodiment, the present invention is directed to a single use multi-chamber packaging of said anti-aging composition. In accordance with this embodiment, each chamber of the multi-chamber packaging contains a separate composition or portion of the anti-aging skin care composition of the present invention. These separate compositions or portions can be mixed prior to use, to form the anti-aging skin care composition of the present invention, prior to application to the skin for the reduction and/or prevention of age-related skin symptoms.

In yet another embodiment, the present invention is directed to an anti-aging kit comprising at least two or more single use multi-chamber packets, each having at least two chambers or compartments for containing separate compositions or portions of the anti-aging skin care composition of the present invention. These separate compositions or portions can be mixed, to form the anti-aging skin care composition of the present invention, prior to application to the skin for the reduction and/or prevention of age-related skin symptoms. In accordance with one aspect of this embodiment, a first multi-chamber packet and a second multi-chamber packet contain at least one active, wherein said active is present at a higher concentration in said second multi-chamber packet. In accordance with another aspect of this embodiment, a second multi-chamber packet contains at least one active agent for reducing and/or preventing age-related skin symptoms, which was not included in the anti-aging composition of the first multi-chamber packet.

DETAILED DESCRIPTION OF THE INVENTION

Figure 1:
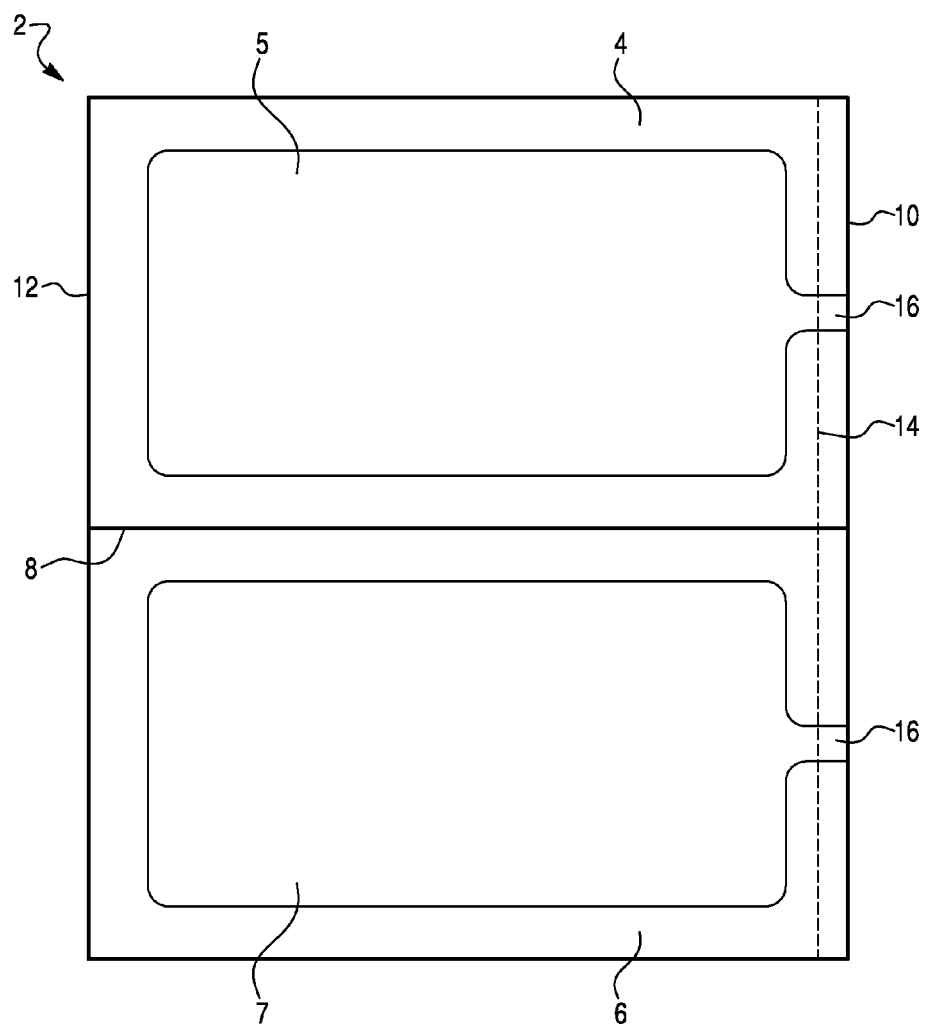
FIG. 1 is a perspective view of a multi-chambered anti-aging packet containing two separate chambers, in accordance with the present invention.

The present invention is directed to a skin care composition and dispensable packaging for use in improving the condition or appearance of skin by preventing, reducing and/or treating the appearance and/or symptoms of skin aging. More specifically, the skin care composition of the present invention is an anti-aging composition which consists of at least two active agents packaged in separate chambers of a single use squeezable or compressible multi-chamber packet. In accordance with the present invention, the single use multi-chamber packet can be opened, the contents emptied (for example, into the user's palm) and mixed just prior to application to skin. The present invention further provides one or more anti-aging kits that are useful for preventing, delaying, reducing and/or treating the consequences of aging on the condition or appearance of the skin.

In one embodiment of the present invention, there is also provided a method for reducing and/or preventing age-related skin symptoms, comprising topically applying an anti-aging skin care composition according to the present invention on human skin. In accordance with this embodiment, each chamber of a single use multi-chamber packet contains a separate composition or portion of the anti-aging skin care composition of the present invention. These separate compositions or portions can be mixed prior to use, to form the anti-aging skin care composition of the present invention, and applied to the skin for the reduction and/or prevention of age-related skin symptoms.

In another embodiment of the present invention, there is also provided an anti-aging kit comprising at least two or more single use multi-chambered packets, for example, a first and second single use multi-chamber packet each containing a portion of the anti-aging skin care composition, wherein the second multi-chamber packet has at least one active agent which is present in a higher concentration than that same active agent is in the first multi-chambered packet. In yet another embodiment, there is provided a method for reducing and/or preventing age-related skin symptoms, comprising topically applying the anti-aging composition of the first multi-chamber packet and subsequently topically applying the anti-aging composition of the second multi-chamber packet. The single use multi-chambered packets can be formulated such that the anti-aging skin care composition of the first multi-chambered packet and second multi-chambered packet can be applied sequentially. This sequential application of two anti-aging skin care compositions allows for one of the two formulations to contain one or more active agents at a higher concentration and/or one or more additional active agents.

As used herein, "reducing and/or preventing age-related skin symptoms" means preventing, delaying, reducing and/or otherwise treating the skin to improve the condition or appearance of skin symptoms (for example, wrinkles, sagging, discoloration, dry skin, etc.) caused from the impact of time and/or environmental influences. In accordance with the present invention, an anti-aging composition can be applied to the skin to provide one or more benefits to the skin, including, but not limited to: treating, delaying or preventing wrinkling; treating, delaying or preventing sagging; treating, delaying or preventing dry skin; treating, delaying or preventing photodamaged skin; treating, delaying or preventing formation of pimples or blackheads; closing pores; promoting the repair of damaged skin; imparting a youthful appearance to skin; imparting fullness to lips; enhancing collagen deposition in skin; enhancing decorin production in skin; enhancing tissue repair; soothing irritated, red or sensitive skin; improving skin texture, smoothness or firmness; normalizing skin color by lightening or darkening skin; and/or limiting oil/sebum secretion.

The inventive compositions, packets, methods and uses described herein result in the prevention, reduction or delay in the formation of wrinkles, the prevention, reduction or delay in loss of skin tone, and the prevention, reduction or delay in the formation of pimples and blackheads. The compositions, methods and uses described herein also moderate skin discolorations such as brown spots, age spots or liver spots, rejuvenate dry, abused, or irritated skin, close or tighten pores, improve skin texture, smoothness or firmness, and create smooth and supple skin with improved elasticity. A general improvement in the appearance, texture and condition, in particular with respect to the radiance, clarity, and general youthful appearance of skin is achieved. The present invention therefore provides a wide range of results that are collectively described as anti-aging benefits.

In one embodiment, the present invention is directed to anti-aging skin care composition for reducing and/or preventing age-related skin symptoms. The anti-aging skin care composition of the present invention comprises at least two separate portions, each containing one or more known active agents to treat the signs of aging by preventing, delaying, reducing and/or otherwise treating the skin to improve the condition or appearance of the skin. In another embodiment, the anti-aging skin care composition of the present invention may contain at least three, at least four, at least five, etc., separate portions, each containing one or more known active agents to treat the signs of aging in accordance with this invention. For example, each separate portion of the anti-agent skin care composition of the present invention can include, but is not limited to, one or more depigmentors, anti-oxidants (including hormonal anti-oxidants), cell lubricants, skin debridements, emollients, skin peels (including chemical skin peels), solvents, humectants, and moisturizers.

The anti-aging skin care composition of the present invention may contain one or more depigmentors, including but not limited to, hydroquinone, hydroquinine, kojic acid, azelaic acid, monobenzone, hydroxyanizole, arbutin, and mixtures thereof. The depigmentor can comprise from about 0.25 wt. % to about 20 wt. % of the final anti-aging composition. In another embodiment, the depigmentor can comprise from about 0.5% to about 10% of the final anti-aging composition.

The anti-aging skin care composition of the present invention may contain one or more anti-oxidant, including but not limited to, cystamine, melatonin, ascorbic acid, alpha-lipoic acid, coenzyme Q, vitamin D, vitamin E, and mixtures thereof. The anti-oxidant of the anti-aging composition can comprise from about 0.5 wt. % to The anti-aging skin care composition of the present invention may contain one or more chemical peeling agents, including but not limited to, glycolic acid, retinoic acid, phenol, phytic acid, acetic acid, lactic acid, and mixtures thereof.

The anti-aging skin care composition of the present invention may also contain one or more moisturizers. Typically, any known moisturizer can be used, including but not limited to, propylene glycol, butylene glycol, hexylene glycol, sorbitol, aloe vera, and mixtures thereof.

Other agents can include, but are not limited to, one or more cell lubricants (for example, silicone), skin debridements (for example, papain), emollients (for example, urea), skin cell regenerators (for example, cystamine, kinetin, or vitamin D), skin cell softeners (for example, DHEA (Dehydriepiandrosterone)), solvents (for example, DMSO), humectants (for example, glycerin), and mixtures thereof.

Preferably, the pharmaceutical composition may further includes a pharmaceutically acceptable carrier such as a cream, gel, lotion, aerosol spray, salve, or infused bandage. Advantageously, the composition is formulated for topical administration.

In some embodiments, it may be advantageous to separate certain agents of the anti-aging skin care composition of the present invention into different portions so that they can be stored separately. By separating some of the agents of the anti-aging skin care composition of the present invention into separate portions, the anti-aging skin care composition of the present invention may result in improved ease of use, stability, and/or efficacy. For example, in some embodiments it may be preferred to provide a formulation in which the moisturizer and the peeling agent are separated into different portions of the anti-aging composition. In other embodiments, it may be preferred to provide a formulation in which the moisturizer and the depigmentor are separated into different portions of the anti-aging composition. In yet other embodiments, it may be preferred to provide a formulation in which the anti-oxidant and the peeling agent or depigmentors are separated into different portions of the anti-aging composition. These separate portions or compositions can be mixed prior to use, to form the anti-aging skin care composition of the present invention, and applied to the skin for the reduction and/or prevention of age-related skin symptoms.

The present invention is also directed to a single use multi-chamber packet for packaging and/or storage of the anti-aging skin care composition of the present invention. In accordance with this embodiment, a multi-chamber packet is provided that has at least two chambers or compartments each containing a separate portion of an anti-aging skin care composition. According to the method of the present invention, the multi-chambered packet can be opened, the contents of the chambers emptied or squeezed out and mixed prior to being applying to ones skin for reducing and/or preventing age-related skin symptoms.

The single use multi-chamber packet of the present invention may facilitate ease of use, long-term storage, and/or efficacy of the anti-aging skin care composition. In other embodiments, an anti-aging composition in accordance with this invention can be produced to contain at least two, at least three, at least four, etc., separate portions, which can be packaged in separate chambers of a single use multi-chambered packet.

The single use multi-chamber packets of the present invention can be more clearly understood from the drawings.

FIG. 1 shows a perspective view of a single use multi-chambered anti-aging packet 2 containing two separate sections 4, 6, each containing therein two chambers 5, 7, in accordance with the present invention. In general, the multi-chambered packet 2 of the present invention can be made of any known material. For example, the multi-layered packet can be made of a metal or plastic foil, with the chambers 5, 7 being formed between two or more layers of foil. As shown in FIG. 1, the two separate sections 4, 6, which extend parallel to each other and having a front edge 10 and a rear edge 12. A flexible seam 8, runs longitudinally from the front edge 10 and the rear edge 12, separating the two sections 4, 6. The single use multi-chamber packet 2 has a common score line or tear line 14, which extends along the front edge 10 of the two separate sections 4, 6, parallel to the front edge 10. The score line or tear line 14 defines a strip 15, which can be peeled or torn away from the multi-chambered packet 2 to expose a channel open 16 and thereby provide access to the interior of chambers 5, 7. Once the strip 15 has been removed the contents of the chambers 5, 7 can be simultaneously emptied (for example, into the palm of a user's hand) and mixed prior to application to the skin. The flexible seam 8 allows the two separate sections 4, 6 to be folded one on top of the other, to allow for ease of use in simultaneously emptying both chambers 5, 7 by squeezing.

Figure 2:
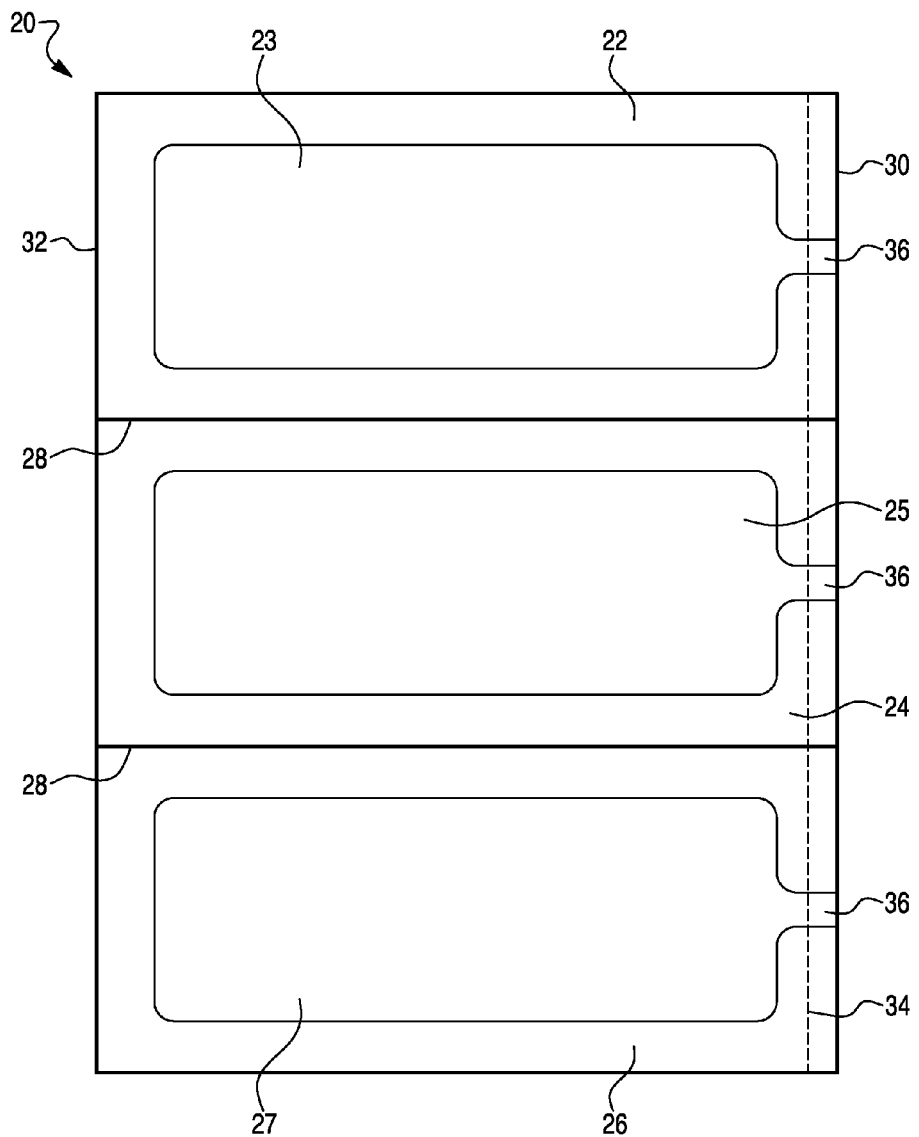
FIG. 2 is a perspective view of a multi-chambered anti-aging packet containing three separate chambers, in accordance with the present invention.

FIG. 2 is a perspective view of a multi-chambered anti-aging packet 20 containing three separate sections 22, 24, 26, each containing therein two chambers 23, 25, 27, in accordance with the present invention. As seen in FIG. 2, the multi-chamber packet 20 of the present invention may contain three separate chambers or compartments 22, 24, 26, which are molded from a metal or plastic foil and extend parallel to each other and having a front edge 30 and a rear edge 32. Two flexible sealing seams 28, 29, run longitudinally from the front edge 30 to the rear edge 12, separating the three chambers 22, 24, 26, respectively. The single use multi-chamber packet 2 has a common score line or tear line 34, which extends through and along each of the separate chambers 22, 24, 26. The score line or tear line 34 defines a strip 35, which can be torn away or removed from the packet 2 to expose a channel open 36 and thereby provide access to the interior of chambers 22, 24, 26. Once the strip 35 has been removed the contents of the chambers 22, 24, 26 can be simultaneously emptied (for example, into the palm of a user's hand) and mixed prior to application to the skin.

Figure 3:
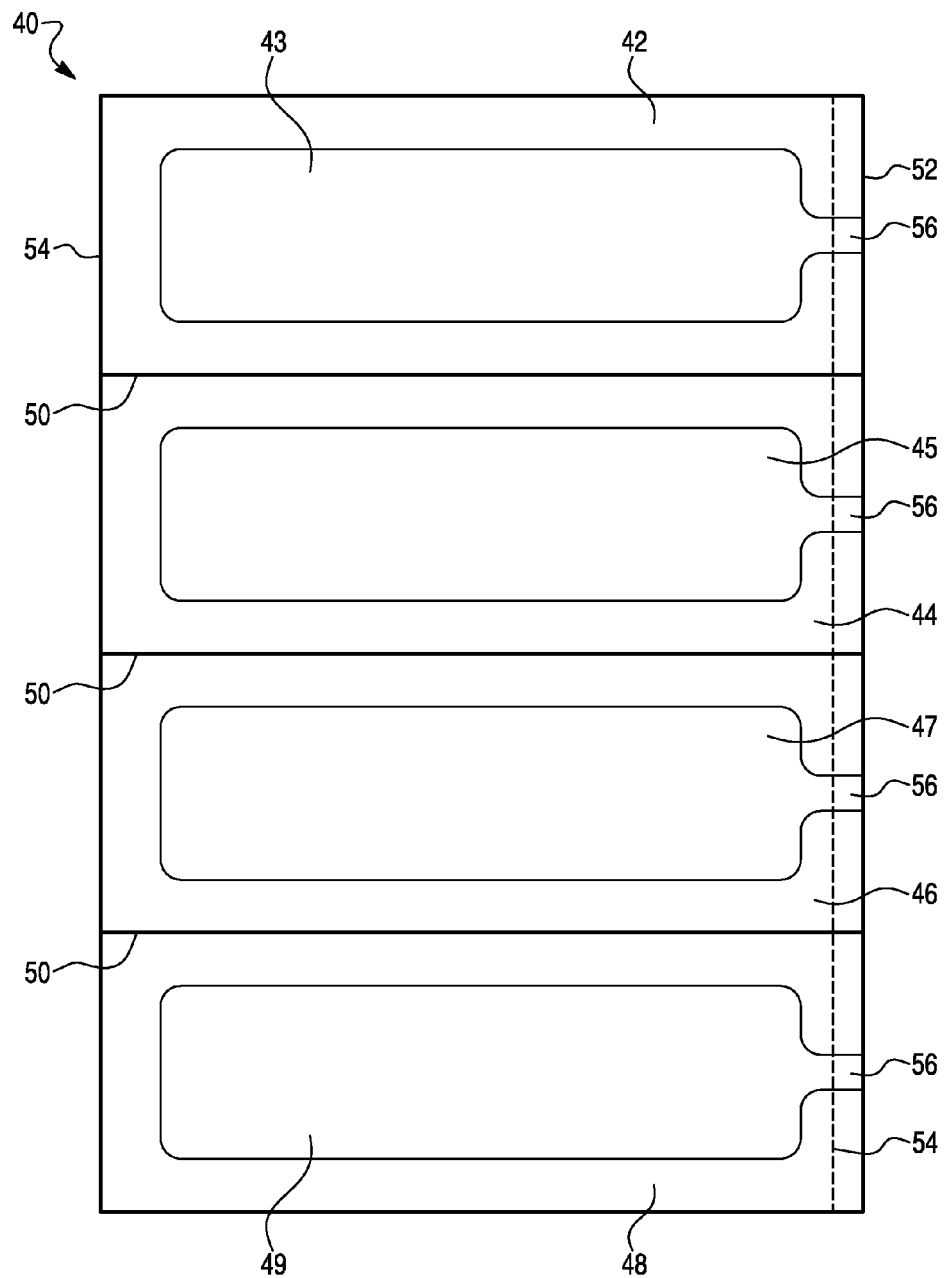
FIG. 3 is a perspective view of a multi-chambered anti-aging packet containing four separate chambers, in accordance with the present invention.

FIG. 3 is a perspective view of a multi-chambered anti-aging packet 40 containing four separate sections 42, 44, 46, 48, each containing therein two chambers 43, 45, 47, 49, in accordance with the present invention. As seen in FIG. 1, the multi-chamber packet 40 of the present invention may contain four separate chambers or compartments 42, 44, 46, 48, which are molded from a metal or plastic foil and extend parallel to each other and having a front edge 50 and a rear edge 52. Three flexible sealing seams 49, 51, 53, run longitudinally from the front edge 50 and the rear edge 52, separating the two chambers 42, 44, 46, 48. The packet 2 has a common score line or tear line 54, which extends through and along each of the separate chambers 42, 44, 46, 48. The score line or tear line 54 defines a strip 55, which can be torn away or removed from the packet 2 to expose a channel open 56 and thereby provide access to the interior of chambers 42, 44, 46, 48. Once the strip 55 has been removed the contents of the chambers 42, 44, 46, 48, can be simultaneously emptied (for example, into the palm of a user's hand) and mixed prior to application to the skin.

The present invention also provides an anti-aging kit for reducing and/or preventing age-related skin symptoms. The anti-aging kit of the present invention provides a convenient anti-aging skin treatment whereby at least two or more multi-chambered packets are provided with different anti-aging compositions. In this manner, a first mild anti-aging composition can be provided in a first set of multi-chambered packets and a second stronger anti-aging composition can be provided in a second set of multi-chambered packets. By first applying the first mild anti-aging composition to the skin, and subsequently applying the second stronger anti-aging composition to the skin, side effects (such as, irritation and/or burning) can be minimized or avoided because the skin is allowed time to adjust to the anti-aging active agent(s) prior to the use of stronger compositions which may cause such side effects.

In accordance with this embodiment, an anti-aging kit is provided wherein said kit comprises at least two or more single use multi-chamber packets, each containing an anti-aging skin care composition, wherein one packet (e.g., a first packet) contains a different anti-aging skin care composition (e.g., a first anti-aging composition) than another packet (e.g., a second packet containing a second anti-aging composition). In accordance with this embodiment, a second anti-aging composition contained in a second packet may have one or more active agents at a higher concentration than the concentration of said one or more agents in a first anti-aging composition contained in a first packet. In an alternative embodiment, the second anti-aging composition of the second packet may have one or more additional anti-aging active agents than the first anti-aging composition of the first packet. For example, an anti-aging kit in accordance with the present invention may comprise two or more different anti-aging skin care compositions. In a first multi-chamber packet a first anti-aging skin care composition is contained having one or more active agents, as described hereinabove, and in a second multi-chamber packet a second anti-aging skin care composition containing therein has the same active agents, wherein one or more actives is at a higher concentration than in the first multi-chambered packet. Such kits may facilitate ease of use, long-term storage, and/or efficacy of the anti-aging skin care composition.

In one embodiment of the present invention, there is provided an anti-aging kit comprising at least two single use multi-chambered packets, for example, a first and second multi-chamber packet each containing an anti-aging skin care composition, wherein the second anti-aging composition of the second multi-chamber packets has at least one active agent which is present at a higher concentration than in the first anti-aging composition in the first multi-chambered packet. In other embodiments, it is possible to provide at least three, at least four, at least five, etc., single use multi-chamber packets (containing, for example, at least three, at least four, at least five, etc., different anti-aging compositions wherein at least one active agent is at progressively higher concentrations in the third, fourth, fifth, etc. multi-chamber packet).

In another embodiment, there is provided a method for reducing and/or preventing age-related skin symptoms, comprising topically applying the anti-aging compositions of the anti-aging kit of the present invention. In accordance with this embodiment, the anti-aging compositions of the at least two, at least three, at least four, at least five, etc., multi-chamber packets are applied to the skin in a sequential order. The multi-chambered packets can be formulated such that the anti-aging skin care composition of the first multi-chambered packet and second multi-chambered packet can be applied sequentially. This sequential application of two anti-aging skin care compositions allows for one of the two formulations to contain one or more active agents at a higher concentration and/or one or more additional active agents.

According to the method of the present invention, the anti-aging kit provides at least two multi-chambered packets containing different anti-aging compositions, which can be opened, the contents of the chambers emptied or squeezed out and mixed prior to being applying to ones skin for reducing and/or preventing age-related skin symptoms. In accordance with this embodiment, the anti-aging skin care composition of a first multi-chamber packet is applied prior to the anti-aging skin care composition of a second multi-chambered packet. The application of the anti-aging skin care composition of the second multi-chambered packet can immediately following the application of the anti-aging skin care composition of the first multi-chambered packet. Alternatively, the anti-aging care composition of the second multi-chamber packet can be applied days, weeks, or even months after the anti-aging composition of the first multi-chamber packet.

For example, it is contemplated that an anti-aging kit may be prepared wherein the kit comprises a first, a second and a third regimen of anti-aging compositions to be applied sequentially to the skin. The first, second and third regimens comprising a first, second and third anti-aging composition, respectively, each regimen consisting of two or more multi-chambered packets containing said first, second and third anti-aging composition, respectively. In accordance with this embodiment, a first set of single use multi-chambered packets each containing a mild anti-aging composition (a first anti-aging composition) can be applied to the skin (for example, once daily) for about 1 week to about 3 weeks. Then a second set of single use multi-chambered packets each containing a moderate anti-aging composition (a second anti-aging composition) can be applied to the skin (for example, once daily) for about 1 week to about 3 weeks. Finally, a third set of single use multi-chambered packets each containing a strong anti-aging composition (a third anti-aging composition) can be applied to the skin (for example, once daily) for about 1 week to about 3 weeks. In this manner, the mild anti-aging composition of the first multi-chambered packet allows the user's skin to adapt to treatment before a second moderate anti-aging composition and finally a stronger anti-aging composition are applied to the skin, thereby reducing skin irritation and sequentially providing increased efficacy.

The anti-aging kits of the present invention, may provide one or more advantages, including but not limited to, providing steps of sequentially stronger anti-aging components and/or providing different compositions for treating different age-related skin symptoms.

The multi-chamber packets of the present invention can be more clearly understood from the drawings.

Figure 4:
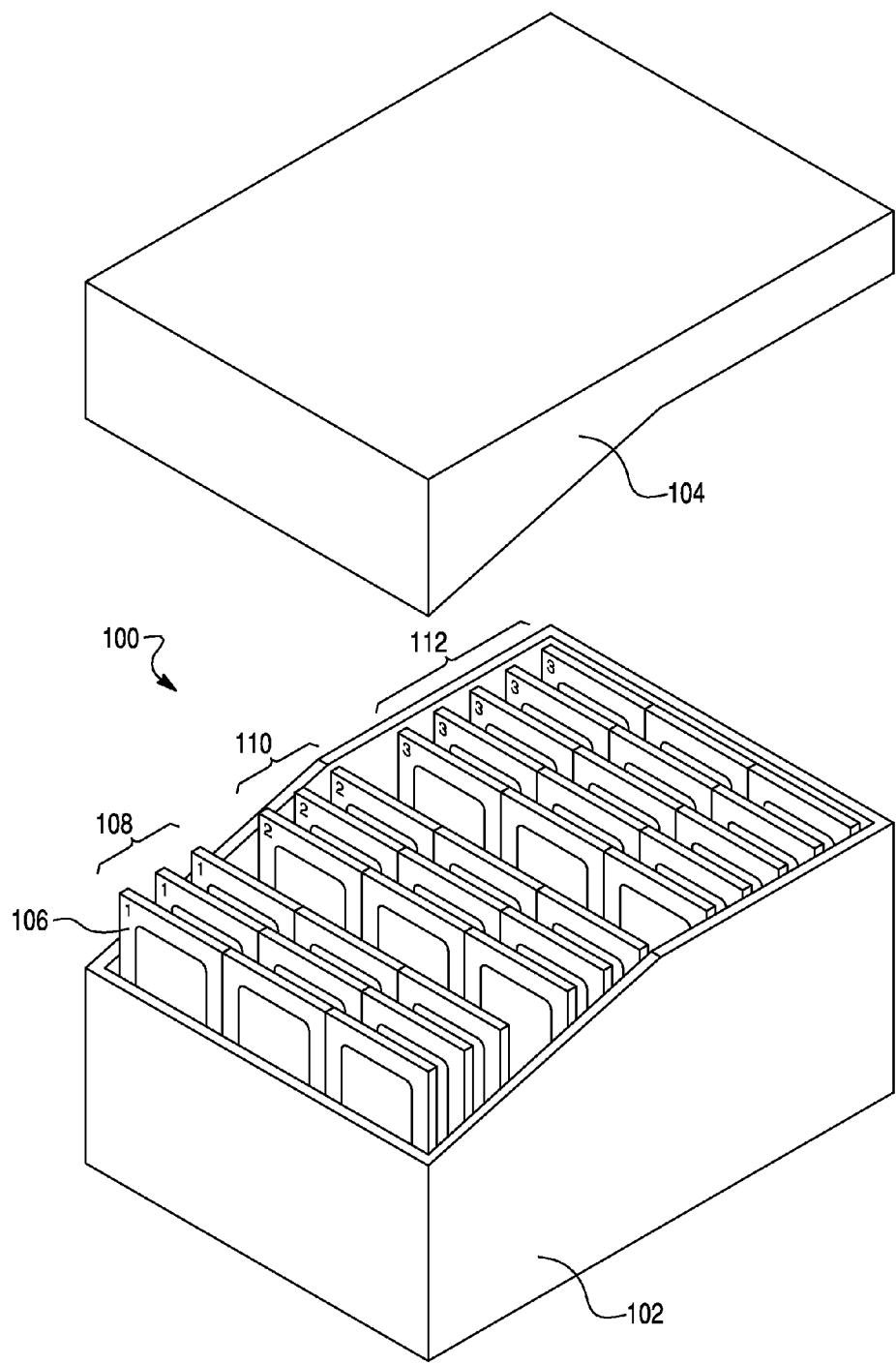
FIG. 4 is a perspective view of an anti-aging kit, in accordance with the present invention.

FIG. 4 shows a perspective view of an anti-aging kit 100. In accordance with the present invention, the kit comprises a box 102, a box lid 104, the box 102 housing more than one multi-chambered packets 106. As shown, the kit comprises three different sets of multi-chambered packets 108, 110, 112, having a first, second and third anti-aging composition contained therein, respectively, for use in the treatment or prevention of age-related skin symptoms. In one embodiment, the first, second and third anti-aging compositions may each contain the same active agent, or set of active agents at different concentrations. For example, the first set of multi-chambered packets 108 may contain a first anti-aging composition, which contains at least one active agent at a lower concentration than found in the second and third multi-chamber packets 110, 112. The first anti-aging composition of the first set of multi-chambered packets 108 may be applied to the skin for the treatment or prevention of age-related skin symptoms over a period of days or longer (for example, over a three day period or more), which allows the skin to adjust or become accustom to the treatment. Subsequently, the second anti-aging composition contained in the second set of multi-chamber packets 110, may be applied to the skin for the treatment or prevention of age-related skin symptoms over a period of days or longer (for example, over a three day period or more). The second anti-aging composition contains at least one active agent at a higher concentration than in said first anti-aging composition, thereby providing improved anti-aging benefits compared to the first anti-aging composition. Finally, the third anti-aging composition contained in the third set of multi-chamber packets 112, may be applied to the skin for the treatment or prevention of age-related skin symptoms over a period of days or longer (for example, over a three day period or more). The third anti-aging composition contains at least one active agent at a higher concentration than in said first and second anti-aging compositions, thereby providing improved anti-aging benefits compared to the first and second anti-aging compositions. As shown, each set of multi-chamber packets of the kit can be labeled (for example, numbered 1, 2, 3, etc.) for convenient use.

What is claimed is:

1. An anti-aging product comprising, at least two active agents for reducing age-related skin symptoms, wherein said at least two active agents are packaged into separate compartments of a single use multi-chamber packet and said at least two active agents are different from each other and interact together, causing one or both to be degraded and/or lose efficacy over time, wherein said multi-chamber packet contains a removable strip which runs through each of said at least two chambers, and wherein said packet has a tear line which allows said strip to be torn away thereby providing access to the interior of chambers.

2. The anti-aging product of claim 1, wherein said at least two active agents are selected from the group consisting of depigmentors, anti-oxidants, cell lubricants, skin debridements, emollients, skin peels, humectants, and moisturizers.

3. The anti-aging product of claim 1, wherein at least one of said active agents is a skin peel agent.

4. The anti-aging product of claim 1, wherein said single use multi-chamber packet contains two chambers.

5. The anti-aging product of claim 1, wherein said single use multi-chamber packet contains three chambers.

6. The anti-aging product of claim 1, wherein said single use multi-chamber packet contains four chambers.

7. The anti-aging product of claim 1, wherein said multi-chamber packet is made of a squeezable or compressible metal or plastic foil.

8. The anti-aging product of claim 1, wherein said single use multi-chamber packet has a tear away or peel away strip which can be removed to thereby provide access to the interior of the chambers of said multi-chamber packet.

9. The anti-aging product of claim 8, wherein each of said chambers has a channel opening which is exposed when said strip is peeled away or torn.

10. A method for reducing age-related skin symptoms, said method comprising, applying an anti-aging composition in the form of at least two active agents to the skin, said agents being divided into at least two separate chambers of a single use multi-chambered packet, wherein said at least two active agents are different from each other and interact together, causing one or both to be degraded and/or lose efficacy over time, and the contents of said single use multi-chambered packet are emptied or squeezed out onto the skin.

11. The method of claim 10, wherein said skin symptoms is selected from the group consisting of reducing wrinkles, sagging, discoloration, dry skin, photodamaged skin formation of pimples or blackheads, closing pores, promoting the repair of damaged skin, enhancing tissue repair, soothing irritation, improving skin texture, improving skin smoothness and improving skin firmness.

* * * * *